United States Patent [19]

Cook

[11] Patent Number: 6,017,895
[45] Date of Patent: Jan. 25, 2000

[54] OLIGONUCLEOTIDES POSSESSING ZWITTERIONIC MOIETIES

[75] Inventor: Alan Frederick Cook, Cedar Grove, N.J.

[73] Assignee: Genzyme Corporation, Framingham, Mass.

[21] Appl. No.: 07/833,146

[22] Filed: Feb. 10, 1992

[51] Int. Cl.[7] .................. A61K 31/715; A61K 38/04; C07H 21/00; C07H 21/04
[52] U.S. Cl. .................. 514/44; 514/2; 536/24.5; 530/300
[58] Field of Search .................. 536/27; 530/300; 562/553, 433; 514/2, 44

[56] References Cited

FOREIGN PATENT DOCUMENTS 0273085  7/1988  European Pat. Off. .

OTHER PUBLICATIONS

Cheng et al. Nucl. Acids Res. 11(3):659–669, 1983.

Primary Examiner—Gary L. Kunz
Attorney, Agent, or Firm—Elliot M. Olstein; Raymond J. Lillie

[57] ABSTRACT

An oligonucleotide wherein at least one nucleotide unit includes a phosphonate moiety having the following structural formula:

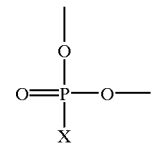

, wherein X is a zwitterionic moiety. Such oligonucleotides have improved cellular uptake capabilities and improved resistance against nuclease activity.

12 Claims, No Drawings

OLIGONUCLEOTIDES POSSESSING ZWITTERIONIC MOIETIES

This invention relates to oligonucleotides which bind to molecules which include RNA (such as mRNA), DNA, proteins, or peptides, including, for example, oligonucleotides which inhibit mRNA function. More particularly, this invention relates to oligonucleotides in which one or more of the nucleotides include a zwitterionic moiety.

Watson-Crick base pairing enables an oligonucleotide to act as an antisense complement to a target sequence of an mRNA in order to block processing or effect translation arrest and regulate selectively gene expression. (Cohen, *Oligodeoxynucleotides*, CRC Press, Boca Raton, Fla. (1989)); Uhlmann, et al., *Chem. Rev.*, Vol. 90, pgs. 543–584 (1990)). Oligonucleotides have also been utilized to interfere with gene expression directly at the DNA level by formation of triple-helical (triplex) structures in part through Hoogsteen bonding interactions (Moffat, *Science*, Vol. 252, pgs 1374–1375 (1991)). Furthermore, oligonucleotides have been shown to bind specifically to proteins (Oliphant, et al., *Molec. Cell. Biol.* Vol 9, pgs. 2944–2949 (1989)) and could thus be used to block undesirable protein function.

Natural oligonucleotides, which are negatively charged, however, are relatively ineffective as therapeutic agents due to their poor penetrability into the cell, and their susceptibility to degradation by nucleases in vivo. Therefore, relatively high concentrations of natural oligonucleotides are required in order to achieve a therapeutic effect.

To overcome the above shortcomings, various strategies have been devised. U.S. Pat. No. 4,469,863, issued to Miller, et al., discloses the manufacture of nonionic nucleic acid alkyl and aryl phosphonates, and in particular nonionic nucleic acid methyl phosphonates. U.S. Pat. No. 4,757,055, also issued to Miller, et al., discloses a method for selectively controlling unwanted expression of foreign nucleic acid in an animal or in mammalian cells by binding the nucleic acid with a nonionic oligonucleotide alkyl or aryl phosphonate analogue.

Oligonucleotides have also been synthesized in which one non-bridging oxygen in each phosphodiester moiety is replaced by sulfur. Such analogues sometimes are referred to as phosphorothioate (PS) nucleotide analogues, or "all PS" analogues, (Stein, et al., *Nucl. Acids Res.*, Vol. 16, pgs. 3209–3221 (1988)). Oligonucleotide phosphorodithioates in whch both non-bridiging oxygen atoms attached to phosphorus are replaced by sulfur, have also been prepared. (Brill, et al. *J. Amer. Chem. Soc.*, Vol. 111, pg. 2321 (1989)). Other backbone-modified oligonucleotides previously prepared include phosphoramidates in which non-bridging oxygen atoms have been replaced by nitrogen. (Froehler, et al., *Nucleic Acids Res.*, Vol. 16, pgs. 4831–4839 (1988)). These compounds, however, are generally less stable due to the presence of labile phosphorus-nitrogen bonds.

Backbone modifications have also been made in which the phosphorus atoms are replaced by other atoms such as carbon or silicon. Examples of such oligonucleotides include oligonucleotide carbamates (Stirchak, et al, *J. Org. Chem*, Vol. 52, pgs. 4202–4206 (1987)), and silyl esters (Cormier, et al., *Nucleic* Acids Res., Vol. 16, pg. 4583 (1988)). A review of modified oligonucleotides previously synthesized is given in Uhlmann, et al., *Chemical Reviews*, Vol. 90, pgs. 543–584 (1990).

Examples of oligonucleotides with positive charges have been reported. Letsinger, et al. (*JACS*, Vol. 110, pgs. 4470–4471 (1988)) describe cationic oligonucleotides in which the backbone is modified by the attachment of diamino compounds to give positively-charged oligonucleotides with phosphoramidate linkages. Phosphoramidate linkages, however, are known to be somewhat labile, especially at acidic pH levels, and therefore the cationic group could be lost under certain conditions. Conjugates with the positively charged molecule polylysine have been described by Lemaitre, et al., *Proc. Nat. Acad. Sci.*, Vol. 84, pgs. 648–652 (1987), and have been shown to be more active in cell culture than unmodified oligonucleotides. Polylysine, however, is not a preferred molecule for conjugation due to its relatively high toxicity.

Notwithstanding these previous reports, oligonucleotides with zwitterionic groups attached to the backbone have not hitherto been described or reported.

In accordance with an aspect of the present invention, there is provided an oligonucleotide wherein at least one nucleotide unit of the oligonucleotide includes a phosphate moiety having the following structural formula:

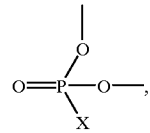

X, wherein X is a zwitterionic moiety. In one embodiment, the zwitterionic moiety is:

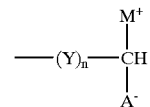

, wherein n is 0 or 1, and Y is:
(Z)p—$R_1$, wherein $R_1$ is a hydrocarbon, preferably an aliphatic hydrocarbon, and more preferably an aliphatic hydrocarbon having from 1 to 15 carbon atoms, p is 0 or 1, and Z is oxygen, sulfur, or $NR_2$, wherein $R_2$ is hydrogen or a hydrocarbon, preferably an aliphatic hydrocarbon, and more preferably an aliphatic hydrocarbon having from 1 to 15 carbon atoms. Preferably, $R_2$ is hydrogen, and $R_1$ is $CH_2$. M+ is:

, wherein each of $R_3$, $R_4$, and $R_5$ is hydrogen or a hydrocarbon, preferably an aliphatic hydrocarbon, and more preferably an aliphatic hydrocarbon having 1 to 15 carbon atoms, and each of $R_3$, $R_4$, and $R_5$ may be the same of different. Preferably, each of $R_3$, $R_4$, and $R_5$ is hydrogen.

$A^-$ is selected from the group consisting of $COO^-$, $SO_3^-$, and $PO_3^{2-}$ The term "oligonucleotide" as used herein means that the oligonucleotide may contain ribonucleotides or deoxyribonucleotides, or both; i.e., the nucleotides in the oligonucleotide may include ribose and/or deoxyribose sugars. Alternatively, the oligonucleotide may include other 5-carbon or 6-carbon sugars, such as, for example, arabinose, xylose, glucose, galactose, or deoxy derivatives thereof.

The oligonucleotides may also include any natural or unnatural, substituted or unsubstituted, purine or pyrimidine base. Such purine and pyrimidine bases include, but are not limited to, natural purines and pyrimidines such as adenine, cytosine, thymine, guanine, uracil, or other purines and pyrimidines, such as isocytosine, 6-methyluracil, 4,6-dihydroxypyrimidine, hypoxanthine, xanthine, azacytosine, 2,6-diaminopurine, 5-methylcytosine, and the like.

In general, the oligonucleotide includes at least two, preferably at least 5, and more preferably from 5 to about 30 nucleotide units.

In another embodiment, the at least one nucleotide unit which has a phosphate moiety substituted with a zwitterionic moiety is one or more nucleotide units at the 3' end and/or the 5' end of the oligonucleotide. In yet another embodiment, nucleotide units which have a phosphate moiety substituted with a zwitterionic moiety as hereinabove described may be nucleotide units which alternate with unsubstituted nucleotide units, and/or with otherwise modified oligonucleotide units. In another embodiment, all of the nucleotide units have a phosphate moiety substituted with a zwitterionic moiety.

The oligonucleotides may also include modified or unmodified phosphorus moieties. The phosphorus moiety may be, for example, a phosphate, phosphonate, alkylphosphonate, aminoalkyl phosphonate, phosphorothioate, phosphoramidate, alkyl phosphonothioate, phosphorodithioate, thiophosphoramidate, phosphotriester and the like. The oligonucleotides may also contain backbone linkages which do not contain phosphorus, such as carbonates, carboxymethyl esters, acetamidates, carbamates, acetals, and the like.

The oligonucleotides may have certain modifications to the 3' or 5' terminus to improve the pharmacological properties of the oligonucleotides, such as amino groups, polyethylene glycol, polylysine, acridine, dodecanol, long chain aliphatic groups and cholesterol.

The oligonucleotides of the present invention may be employed to bind to RNA sequences by Watson-Crick hybridization, and thereby block RNA processing or translation. For example, the oligonucleotides of the present invention may be employed as "antisense" complements to target sequences of mRNA in order to effect translation arrest and regulate selectively gene expression.

The oligonucleotides of the present invention may be employed to bind double-stranded DNA to form triplexes, or triple helices. Such triplexes inhibit the replication or transcription of DNA, thereby disrupting gene transcription. Such triplexes may also protect DNA binding sites from the action of enzymes such as DNA methylases.

The RNA or DNA of interest, to which the oligonucleotide binds, may be present in a prokaryotic or eukaryotic cell, a virus, a normal cell, or a neoplastic cell. The sequences may be bacterial sequences, plasmid sequences, viral sequences, chromosomal sequences, mitochondrial sequences, or plastid sequences. The sequences may include open reading frames for coding proteins, mRNA, ribosomal RNA, snRNA, hnRNA, introns, or untranslated 5'- and 3'-sequences flanking open reading frames. The target sequence may therefore be involved in inhibiting expression of a particular protein, enhancing the expression of a particular protein by inhibiting the expression of a repressor, or the sequences may be involved in reducing the proliferation of viruses or neoplastic cells.

The oligonucleotides may be used in vitro or in vivo for modifying the phenotype of cells, or for limiting the proliferation of pathogens such as viruses, bacteria, protists, Mycoplasma species, Chlamydia or the like, or for inducing morbidity in neoplastic cells or specific classes of normal cells. Thus, the oligonucleotides may be administered to a host subject to or in a diseased state, to inhibit the transcription and/or expression of the native genes of a target cell. Therefore, the oligonucleotides may be used for protection from a variety of pathogens in a host, such as, for example, enterotoxigenic bacteria, Pneumococci, Neisseria organisms, Giardia organisms, Entamoebas, neoplastic cells, such as carcinoma cells, sarcoma cells, and lymphoma cells; specific B-cells; specific T-cells, such as helper cells, suppressor cells, cytotoxic T-lymphocytes (CTL), natural killer (NK) cells, etc.

The oligonucleotides may be selected so as to be capable of interfering with transcription product maturation or expression of proteins by any of the mechanisms involved with the binding of the subject composition to its target sequence. These mechansims may include interference with processing, inhibition of transport across the nuclear membrane, cleavage by endonucleases, or the like.

The oligonucleotides may be complementary to such sequences as sequences encoding growth factors, lymphokines, immunoglobulins, T-cell receptor sites, MHC antigens, DNA or RNA polymerases, antibiotic resistance, multiple drug resistance (mdr), genes involved with metabolic processes, in the formation of amino acids, nucleic acids, or the like, DHFR, etc. as well as introns or flanking sequences associated with the open reading frames.

The following table is illustrative of some additional applications of the subject compositions.

| Area of Application | Specific Application Targets |
| --- | --- |
| Infectious Diseases: | |
| Antivirals, Human | AIDS, Herpes, CMV |
| Antivirals, Animal | chicken Infectious Bronchitis Pig Transmissible Gastroenteritis Virus |
| Antibacterial, Human | Drug Resistance Plasmids, E. coli |
| Antiparasitic Agents | Malaria Sleeping Sickness (Trypanosomes) |
| Cancer | |
| Direct Anti-Tumor Agents | Oncogenes, tumor suppressor genes, and their products |
| Adjunctive Therapy | Drug resistance, genes and their products |
| Auto Immune Diseases | |
| T-celt receptors | Rheumatoid Arthritis Type I Diabetes Systemic Lupus Multiple sclerosis |
| Organ Transplants | Kidney-OTK3 cells cause GVHD |

The oligonucleotides of the present invention may be employed for binding to target molecules, such as, for example, proteins including, but not limited to, ligands, receptors, and/or enzymes, whereby such oligonucleotides inhibit the activity of the target molecules.

The above techniques in which the oligonucleotides may be employed are also applicable to the inhibition of viral replication, as well as to the interference with the expression of genes which may contribute to cancer development.

The oligonucleotides of the present invention are administered in an effective binding amount to an RNA, a DNA, a protein, or a peptide. Preferably, the oligonucleotides are administered to a host, such as a human or non-human animal host, so as to obtain a concentration of oligonucleotide in the blood of from about 0.1 to about 100 $\mu$mole/l. It is also contemplated, however, that the oligonucleotides may be administered in vitro or ex vivo as well as in vivo.

The oligonucleotides may be administered in conjunction with an acceptable pharmaceutical carrier as a pharmaceutical composition. Such pharmaceutical compositions may contain suitable excipients and auxiliaries which facilitate processing of the active compounds into preparations which can be used pharmaceutically. Such oligonucleotides may be administered by intramuscular, intraperitoneal, intravenous, or subdermal injection in a suitable solution. Preferably, the preparations, particularly those which can be administered orally and which can be used for the preferred type of administration, such as tablets, dragees and capsules, and preparations which can be administered rectally, such as suppositories, as well as suitable solutions for administration parenterally or orally, and compositions which can be administered bucally or sublingually, including inclusion compounds, contain from about 0.1 to 99 percent by weight of active ingredients, together with the excipient. It is also contemplated that the oligonucleotides may be administered topically.

The pharmaceutical preparations of the present invention are manufactured in a manner which is itself well known in the art. For example, the pharmaceutical preparations may be made by means of conventional mixing, granulating, dragee-making, dissolving or lyophilizing processes. The process to be used will depend ultimately on the physical properties of the active ingredient used.

Suitable excipients are, in particular, fillers such as sugar, for example, lactose or sucrose, mannitol or sorbitol, cellulose preparations and/or calcium phosphates, for example, tricalcium phosphate or calcium hydrogen phosphate, as well as binders such as starch or paste, using, for example, maize starch, wheat starch, rice starch, potato starch, gelatin, gum tragacanth, methyl cellulose, hydroxypropylmethylcellulose, sodium carboxypropylmethylcellulose, sodium carboxymethylcellulose, and/or polyvinyl pyrrolidone. If desired, distintegrating agents may be added, such as the above-mentinoed starches as well as carboxymethyl-starch, cross-linked polyvinyl pyrrolidone, agar, or alginic acid or a salt thereof, such as sodium alginate. Auxiliaries are flow-regulating agents and lubricants, such as, for example, silica, talc, stearic acid or salts thereof, such as magnesium stearate or calcium stearate, and/or polyethylene glycol. Dragee cores may be provided with suitable coatings which, if desired, may be resistant to gastric juices. For this purpose, concentrated sugar solutions may be used, which may optionally contain gum arabic, talc, polyvinylpyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose phthalate, are used. Dyestuffs and pigments may be added to the tablets of dragee coatings, for example, for identification or in order to characterize different combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the oligonucleotide in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, liquid paraffin, or liquid polyethylene glycols. In addition, stabilizers may be added.

Possible pharmaceutical preparations which can be used rectally include, for example, suppositories, which consist of a combination of the active compounds with a suppository base. Suitable suppository bases are, for example, natural or synthetic triglycerides, paraffin hydrocarbons, polyethylene glycols, or higher alkanols. In addition, it is also posible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble or water-dispersible form. In addition, suspensions of the active compounds as appropriate oil injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension including, for example, sodium carboxymethyl cellulose, sorbitol and/or dextran. Optionally, the suspension may also contain stabilizers.

Additionally, the compounds of the present invention may also be administered encapsulated in liposomes, wherein the active ingredient is contained either dispersed or variously present in corpuscles consisting of aqueous concentric layers adherent to lipidic layers. The active ingredient, depending upon its solubility, may be present both in the aqueous layer, in the lipidic layer, or in what is generally termed a liposomic suspension. The hydrophobic layer, generally but not exclusively, comprises phospholipids such as lecithin and sphingomycelin, steroids such as cholesterol, surfactants such as dicetylphosphate, stearylamine, or phosphatidic acid, and/or other materials of a hydrophobic nature. The diameters of the liposomes generally range from about 15 nm to about 5 microns.

The invention will now be described with respect to the following examples; however, the scope of the present invention is not intended to be limited thereby.

EXAMPLE 1

Synthesis of a Zwitterionic Oligonucleotide via a Phosphorothioate Intermediate

An unmodified oligonucleotide is synthesized on a DNA synthesizer (Applied Biosystems Corp.) using phosphoramidite chemistry with monomers and reagents as supplied by the manufacturer. After completion of fourteen cycles of synthesis, one additional cycle is performed in which the standard iodine oxidation step is replaced by an oxidation reaction us ing tetraethyl thiuram disulfide (TETD). This procedure results in introduction of a phosphorothioate group at the 5'-terminal linkage of the 15 mer. After cleavage of the oligonucleotide from the solid support followed by deprotection with ammonia, the oligonucleotide, which has the following structural formula:

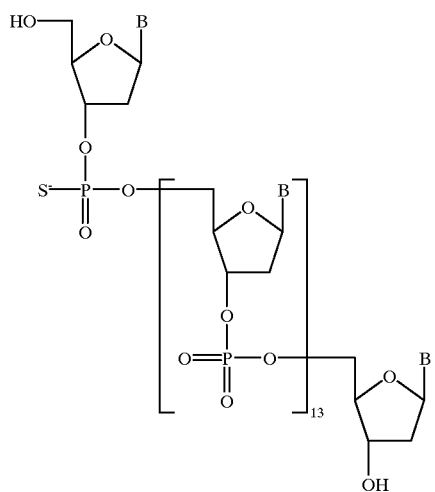

(1)

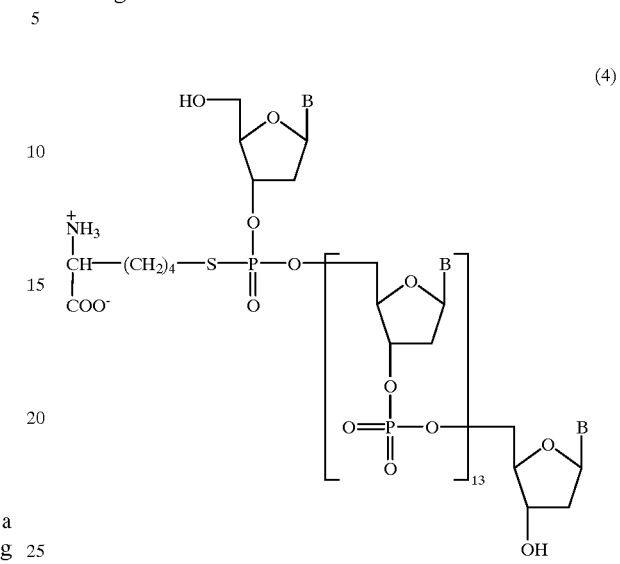

(4)

wherein B is a purine or pyrimidine base, is treated with a protected epsilon-bromo amino acid having the following structural formula:

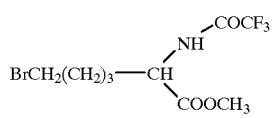

(2)

to produce an S-alkyl derivative having the following structural formula:

Removal of the amino and carboxyl protecting groups with aqueous ammonia generates a zwitterionic group to give a 15-base zwitterionic oligonucleotide having the following structural formula:

EXAMPLE 2

Introduction of a 5'-Zwitterionic Group

An oligonucleotide is prepared on a DNA synthesizer (Applied Biosystems Corp.) using phosphoramidite chemistry with monomers and reagents as supplied by the manufacturer. After completion of fourteen cycles of synthesis, one additional cycle is performed in which a 5'-phosphoryl group is introduced using di-isopropylamino-cyanoethyl phosphine as the monomer. Cleavage from the column and deprotection using aqueous ammonia produces an oligonucleotide having the following structural formula:

(3)

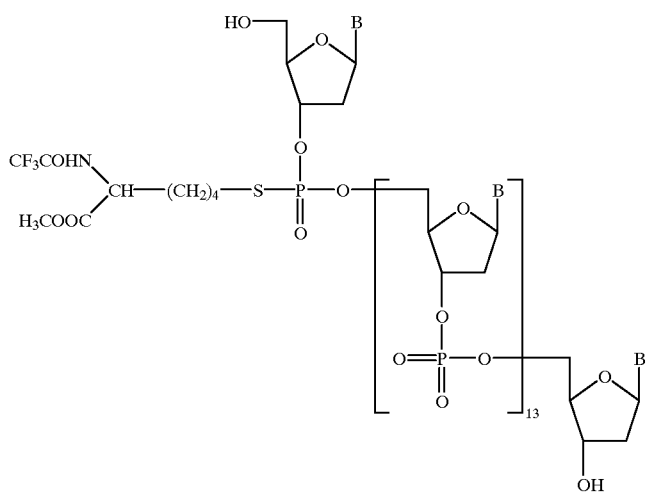

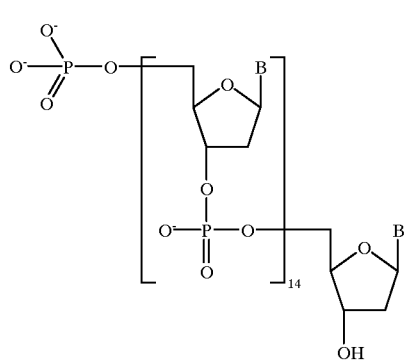

(5)

The oligonucleotide is then coupled with a protected epsilon-hydroxy amino acid having the following structural formula:

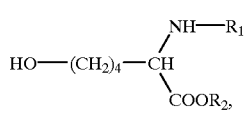

(6)

wherein $R_1$ is carbobenzyloxy and $R_2$ is benzhydryl, and using triisopropylbenzene-sulfonyl triazolide as the coupling agent produces a protected oligonucleotide having the following structural formula:

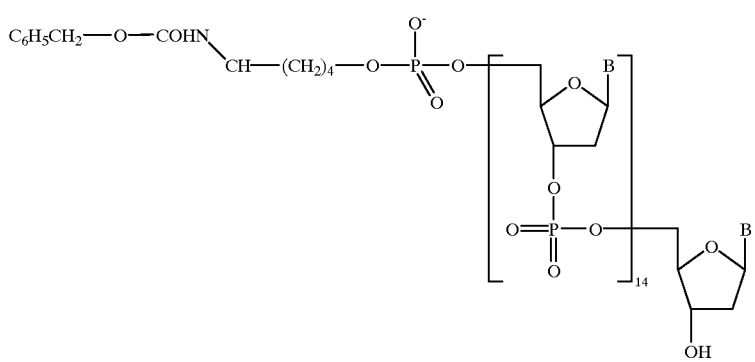

(7)

Removal of the amino and carboxyl protecting groups with hydrogen and palladium on carbon produces an oligonucleotide which possesses a zwitterionic group at the 5'-position and has the following structural formula:

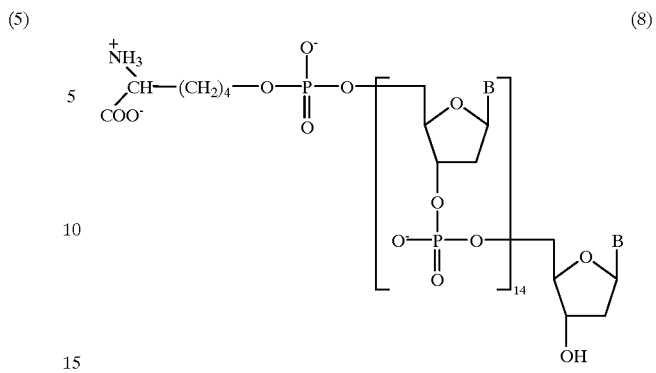

(8)

EXAMPLE 3

Synthesis of an Oligonucleotide with Zwitterionic Groups at each Phosphorus Atom An unmodified oligonucleotide is synthesized on a DNA synthesizer (Applied Biosystems Corp.) using phosphoramidite chemistry with monomers and reagents as supplied by the manufacturer. After completion of fourteen cycles of synthesis, the oligonucleotide is cleaved from the column and deprotected using aqueous ammonia to produce an unmodified 15 base oligonucleotide. This material is reacted with an excess of the protected amino acid (6) using triisopropylbenzenesulfonyl triazolide as the coupling agent.

Removal of the amino and carboxyl protecting groups with hydrogen and palladium on carbon produces an oligonucleotide which possesses a zwitterionic group at each phosphorus atom and which has the following structural formula:

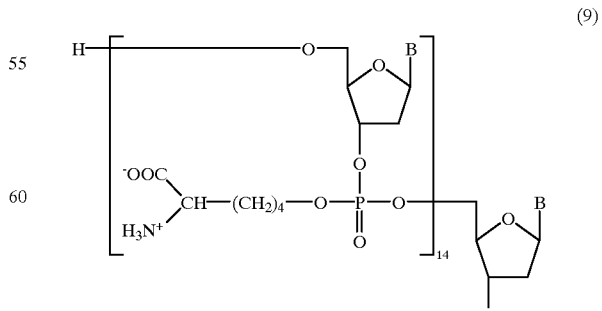

(9)

wherein B is a purine or pyrimidine base.

EXAMPLE 4

Introduction of a 3'-Zwitterionic Group via an Oligonucleotide H-Phosphonate

A dinucleotide is synthesized on a DNA synthesizer (Applied Biosystems Corp.) using H-phosphonate chemistry with monomers and reagents as supplied by the manufacturer. After completion of the coupling, the oxidation of the H-phosphonate intermediate is carried out using a partially protected lysine derivative having the following structural formula:

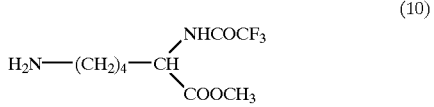
(10)

in place of the standard iodine/water reagent. An additional thirteen cycles of monomer addition are then carried out on the DNA synthesizer, and iodine/water/pyridine is used for the oxidation of the H-phosphonates to phosphodiesters. After cleavage from the column and removal of both the oligonucleotide and amino acid protecting groups, the 15 base oligonucleotide (11) is produced having one zwitterionic group at the 3'-position, and having the following structural formula:

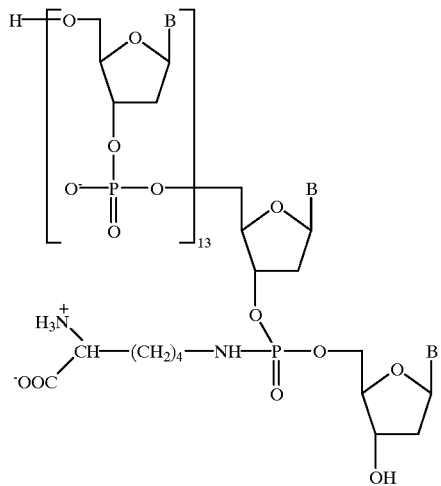

Advantages of the present invention include improved resistance of the zwitterionic oligonucleotide to degradation by nucleases, as compared with natural oligonucleotides which are negatively-charged, and readily degraded by the cell.

In addition, zwitterionic oligonucleotides may be taken up by the cell via receptors, (eg., amino acid receptors) which recognize a zwitterionic group.

It is to be understood, however, that the scope of the present invention is not to be limited to the specific embodiments described above. The invention may be practiced other than as particularly described and still be within the scope of the accompanying claims.

What is claimed is:

1. An oligonucleotide wherein a plurality of nucleotide units thereof include a zwitterionic moiety substitutes phosphate moiety having the formula

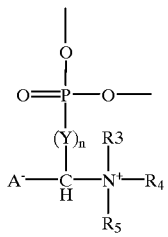

wherein Y is $(Z)_p$—$CH_2$; is 0 or 1; Z is oxygen, sulfur or NH; $R_3$, $R_4$ and $R_5$ are each independently a $C_1$–$C_{15}$ aliphatic hydrocarbon; and A is selected from the group consisting of COO–, $SO_3^-$ and $PO_3^{2-}$.

2. The oligonucleotide of claim 1 wherein each of $R_3$, $R_4$ and $R_5$ are hydrogen.

3. The oligonucleotide of claim 1 which has a zwitterionic moiety substituted phosphate moiety of at least one nucleotide unit at at least one of a 5' or 3' end thereof.

4. The oligonucleotide of claim 1 which has zwitterionic moiety substituted phosphate moieties that alternate with nucleotide units having unsubstituted phosphate moieties.

5. The oligonucleotide of claim 1 in which each of the phosphate moieties is substituted with a zwitterionic moiety.

6. A composition for binding to an RNA, a DNA, a protein or a peptide, comprising (a) an oligonucleotide wherein a plurality of nucleotide units thereof include a zwitterionic moiety substitutes phosphate moiety having the formula

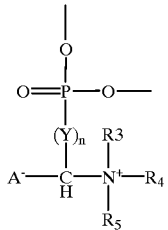

wherein Y is $(Z)_p$—$CH_2$; p is 0 or 1; Z is oxygen, sulfur or NH; $R_3$, $R_4$ and $R_5$ are each independently a $C_1$–$C_{15}$ aliphatic hydrocarbon; and A is selected from the group consisting of COO, $SO_3^-$ and $PO_3^{2-}$; and (b) an acceptable pharmaceutical carrier, wherein said oligonucleotide is present in an effective binding amount to an RNA, a DNA, a protein, or a peptide.

7. The composition of claim 6 wherein each of $R_3$, $R_4$ and $R_5$ are hydrogen.

8. The composition of claim 6 which has a zwitterionic moiety substituted phosphate moiety of at least one nucleotide unit at at least one of a 5' or 3' end thereof.

9. The composition of claim 6 which has zwitterionic moiety substituted phosphate moieties that alternate with nucleotide units having unsubstituted phosphate moieties.

10. The oligonucleotide of claim 6 in which each of the phosphate moieties is substituted with a zwitterionic moiety.

11. An oligonucleotide wherein at least one nucleotide unit of said olignonucleotide includes a phosphate moiety having the following structural formula:

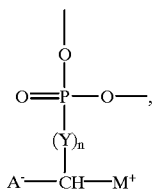

wherein n is 0 or 1; and Y is:

(Z)$_p$—R$_1$, wherein R$_1$ is a hydrocarbon, p is 0 or 1, and Z is oxygen, sulfur, or NR$_2$, wherein R$_2$ is hydrogen or a hydrocarbon; M$^+$ is:

wherein each of R$_3$, R$_4$, and R$_5$ is hydrogen or a hydrocarbon, and each of R$_3$, R$_4$, and R$_5$ may be the same or different, and A– is selected from the group consisting of COO–, SO$^-_3$, and PO$_3^{2-}$.

12. A composition for binding to an RNA, a DNA, a protein, or a peptide, comprising:
(a) an oligonucleotide wherein at least one nucleotide unit of said oligonucleotide includes a phosphate moiety having the following structural formula

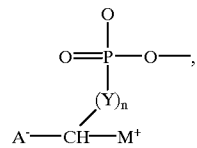

wherein n is 0 or 1, and Y is:

(Z)$^p$—R$_1$, wherein R$_1$ is a hydrocarbon, p is 0 or 1, and Z is oxygen, sulfur, or NR$_2$, wherein R$_2$ is hydrogen or a hydrocarbon; M$_+$ is:

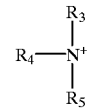

wherein each of R$^3$, R$^4$, and R$^5$ is hydrogen or a hydrocarbon and each of R$^3$, R$^4$, and R$^5$ may be the same or different, and A– is selected from the group consisting of COO–, SO$_3$–, PO$_3^{2-}$ and (b) an acceptable pharmaceutical carrier.

* * * * *